United States Patent [19]

Harrison et al.

[11] Patent Number: 5,536,856

[45] Date of Patent: Jul. 16, 1996

[54] PRODUCTION OF CARBOXYLIC ACID ESTER BY ESTERIFICATION AND APPARATUS THEREOF

[75] Inventors: George E. Harrison, Billericay; John Scarlett, Kirk Merrington; Michael A. Wood, Nunthorpe; Donald H. McKinley, Radlett, all of England

[73] Assignee: Davy Process Technology Limited, London, England

[21] Appl. No.: 200,314

[22] Filed: Feb. 23, 1994

Related U.S. Application Data

[63] Continuation of Ser. No. 721,441, filed as PCT/GB90/00064, Jan. 16, 1990, abandoned.

[30] Foreign Application Priority Data

Jan. 17, 1989 [GB] United Kingdom ............ 8900996
Dec. 18, 1989 [GB] United Kingdom ............ 8928541

[51] Int. Cl.⁶ .................................................... C11C 1/00
[52] U.S. Cl. ........................... 554/164; 554/167; 554/168; 554/170; 261/108; 261/113; 261/114.5
[58] Field of Search .................... 554/168, 170, 554/167; 261/108, 113, 114.5; 560/263; 584/164, 163

[56] References Cited

U.S. PATENT DOCUMENTS 4,381,407  4/1983  Bremus et al. .................. 560/263
5,008,046  4/1991  Bremus et al. .................. 260/410.6

FOREIGN PATENT DOCUMENTS 0255399  2/1988  European Pat. Off. .
2109265  6/1983  United Kingdom .

Primary Examiner—José G. Dees
Assistant Examiner—Deborah D. Carr
Attorney, Agent, or Firm—Rothwell, Figg, Ernst & Kurz

[57] ABSTRACT

Esterification is carried out in a column reactor (14) in which there is a plurality of esterification trays (15) each having predetermined liquid hold-up and containing a charge of a solid esterification catalyst thereon. e.g. an ion exchange resin containing a —$SO_3H$ and/or —COOH groups. A liquid phase containing the carboxylic acid component, e.g. a fatty acid mixture, flows down the column reactor from one esterification tray to the next downward one against an upflowing alcohol vapour stream, e.g. methanol vapour. Relatively dry alcohol vapour is injected (21) into the bottom of the column reactor. Water of esterification is removed from the top of the column reactor in the vapour stream (26), whilst ester product is recovered (23) from the sump of the reactor. As the liquid flows down the trays it encounters progressively drier alocohol and the esterification equilibrium reaction is driven further and further towards 100% ester formation. A polishing reactor (304) operated under liquid phase conditions may follow the column reactor, the ester-containing product from which is mixed with further alcohol before admission to the polishing reactor.

18 Claims, 5 Drawing Sheets

PRODUCTION OF CARBOXYLIC ACID ESTER BY ESTERIFICATION AND APPARATUS THEREOF

This is a continuation of application Ser. No. 07/721,441, filed as PCT/GB90/00064, Jan. 16, 1990 now abandoned.

BACKGROUND

1. Field of the Invention

This invention relates to a process and apparatus for the production of carboxylic acid esters.

2. Description of the Related Art

Esterification is a well known equilibrium limited reaction involving reaction of a mono-, di- or polycarboxylic acid (or, in suitable cases, an acid anhydride) with an alcohol or phenol component. Such an alcohol or phenol component can be mono, di- or polyhydric.

In the formation of a monoester, for example, the reaction can be summarised:

$$R^1COOH + R^2OH \rightleftharpoons R^1COOR^2 + H_2O, \quad (1)$$

where $R^1$ is a hydrogen atom or a monovalent organic radical and $R^2$ is a monovalent organic radical. When an acid anhydride is used as the acid component, the reaction occurs in two stages:

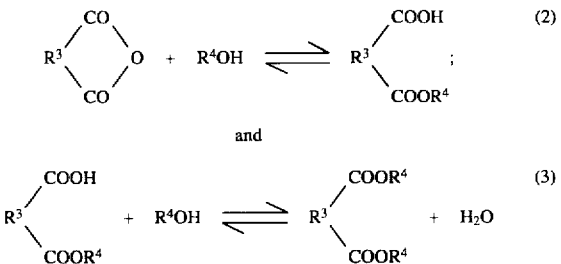

where $R^3$ is a divalent organic radical and $R^4$ is a monovalent organic radical.

Although the reaction of equation (2) above will normally proceed in the absence of added catalyst and although the organic acid may autocatalyse reactions (1) and (3) to some extent, it is normal practice to add a catalyst to the esterification reaction mixture in order to accelerate the reaction.

Perhaps the most widely used catalysts are sulphuric acid and organic sulphonic acids, such as p-toluenesulphonic acid. Although these catalysts are efficient, they are homogeneous catalysts and a neutralisation step is necessary before ester purification can be attempted. Typically washing with an alkali, such as sodium hydroxide solution, is used in such a neutralisation step. As esterification is an equilibrium process, a disadvantage of this procedure is that the washing step also results in removal of any unreacted carboxylic acid component in the wash liquor. Normally it is uneconomic to attempt to recover the unreacted acid from its salt in the wash liquor so that this may represent a significant loss of process efficiency. In addition some ester may be lost in this washing step. The losses of ester in the aqueous alkali phase will depend on the solubility of the ester in such solutions. The sodium salt of a partially esterified polycarboxylic acid will also be soluble in the aqueous alkali liquor. Loss of such partially esterified polycarboxylic acid will, in this case, represent a loss both of acid moieties and also of alcohol moieties. Furthermore the disposal of the wash liquor may present environmental problems which may be aggravated by the presence of the organic carboxylic acid salt in the wash liquor. In addition, particularly when long chain fatty acids are involved, problems may arise in the washing step due to formation of emulsions that are stabilised by the alkali metal fatty acid salts, which are surface active, and that are often difficult to separate into their component aqueous and organic phases. The stability of such emulsions is known to vary in an erratic way, thus making the design of, the organic phase/aqueous phase separation equipment difficult. Therefore it is difficult to practise an esterification process with a homogeneous catalyst on a continuous basis. As a result batch processing is usually adopted, a factor which may affect product quality from batch to batch. An additional disadvantage of the use of such homogeneous catalysts is the risk of contamination of the ester with sulphur-containing components. Such sulphur-containing components can interfere seriously with subsequent chemical processing steps.

Recently there has been proposed, as a result of work carried out in our laboratories, a continuous process for the production of dialkyl maleates which utilises an acidic ion exchange resin as catalyst. This proposal is described in EP-A-0255399 and in WO-A-88/00937. According to this proposal a dialkyl maleate is produced by flowing a liquid feed mixture containing monoalkyl maleate in countercurrent to a flow of vaporous alkanol vapour, so that the liquid phase encounters progressively drier alkanol vapour in passage through the catalyst-containing esterification zone or zones. In one embodiment the resin catalyst is wrapped in mesh packages and packed as a trickle bed in a tower down which the liquid phase flows against an upcoming alcohol vapour. In another embodiment a plurality of continuously stirred tank reactors is used with the liquid phase passing from one reactor to the next succeeding reactor of the series whilst the alcohol vapour flows from each reactor to the preceding reactor of the series.

The proposals described in EP-A-0255399 and in WO-A-88/00937 are somewhat complex. The tower concept requires that the ion exchange resin be wrapped in individual mesh packages. The multi-reactor system requires continuous operation of stirrer motors and is somewhat difficult in practice to control, besides requiring a significant site area for erection.

A form of gas-liquid contact column is described in U.S. Pat. No. 3,394,927. DE-B-1009749 describes a column reactor for hydrogenating unsaturated oils. In FR-A-1384683 there is described a multi-compartment column reactor in which catalytic reactions can be carried out between a gas and a liquid flowing in countercurrent from compartment to compartment and in co-current within each compartment.

SUMMARY OF THE INVENTION

The present invention seeks to produce an improved continuous process for production of esters using ion exchange resin catalysts which is simple in operation and obviates the need to provide continuous mechanical stirring, whilst permitting use of free particulate ion exchange resin.

According to the present invention there is provided a continuous process for the production of carboxylic acid esters by reaction of a carboxylic acid component selected from mono-, di- and polycarboxylic acids, anhydrides thereof, and mixtures thereof, and of an alcohol component selected from mono-, di- and polyhydric alcohols, phenols and mixtures thereof, in which the carboxylic acid component and alcohol component are passed in countercurrent through an esterification zone maintained under esterification conditions and containing a solid esterification catalyst selected from particulate ion exchange resins having sulphonic acid groups, carboxylic acid groups or both, characterised in that the esterification zone comprises a column reactor provided with a plurality of esterification trays mounted one above another, each adapted to hold a predetermined liquid volume and a charge of solid esterification catalyst thereon, liquid downcomer means associated with each esterification tray adapted to allow liquid phase to pass down the column reactor from that esterification tray but to retain solid esterification catalyst thereon, and vapour upcomer means associated with each esterification tray adapted to allow vapour to enter that esterification tray from below and to agitate the mixture of liquid and solid esterification catalyst on that tray, that the less volatile component of the carboxylic acid component and of the alcohol component is supplied in liquid phase to the uppermost one of said plurality of esterification trays whilst the more volatile component of the carboxylic component and of the alcohol component is supplied in vapour form beneath the lowermost one of said plurality of esterification trays, that vapour comprising said more volatile component and water of esterification is recovered from an upper part of the column reactor, and that said carboxylic acid ester is recovered from a lower part of the column reactor.

The invention further provides apparatus for use in the production of a carboxylic acid ester by reaction of a carboxylic acid component selected from mono-, di- and polycarboxylic acids, anhydrides thereof, and mixtures thereof, and of an alcohol component selected from mono-, di- and polyhydric alcohols, phenols and mixtures thereof, comprising a column reactor provided with a plurality of esterification trays mounted one above another, each adapted to hold a predetermined liquid volume and a charge of a solid esterification catalyst thereon, liquid downcomer means associated with each esterification tray adapted to allow liquid phase to pass down the column reactor from that esterification tray but to retain solid esterification catalyst thereon, vapour upcomer means associated with each esterification tray adapted to allow vapour to enter that esterification tray from below and to agitate the mixture of liquid and solid esterification catalyst on that esterification tray, means for supplying the less volatile component of the carboxylic acid component and of the alcohol component in liquid phase to an upper part of the column reactor above the uppermost esterification tray, means for supplying the more volatile component of the carboxylic acid component and of the alcohol component in vapour form to a lower part of the column reactor below the lowermost esterification tray, means for recovering carboxylic acid ester from a lower part of the column reactor below the lowermost esterification tray, and means for recovering from an upper part of the column reactor above the uppermost esterification tray a vaporous stream comprising said more volatile component and water of esterification.

DETAILED DESCRIPTION

Figure 1:
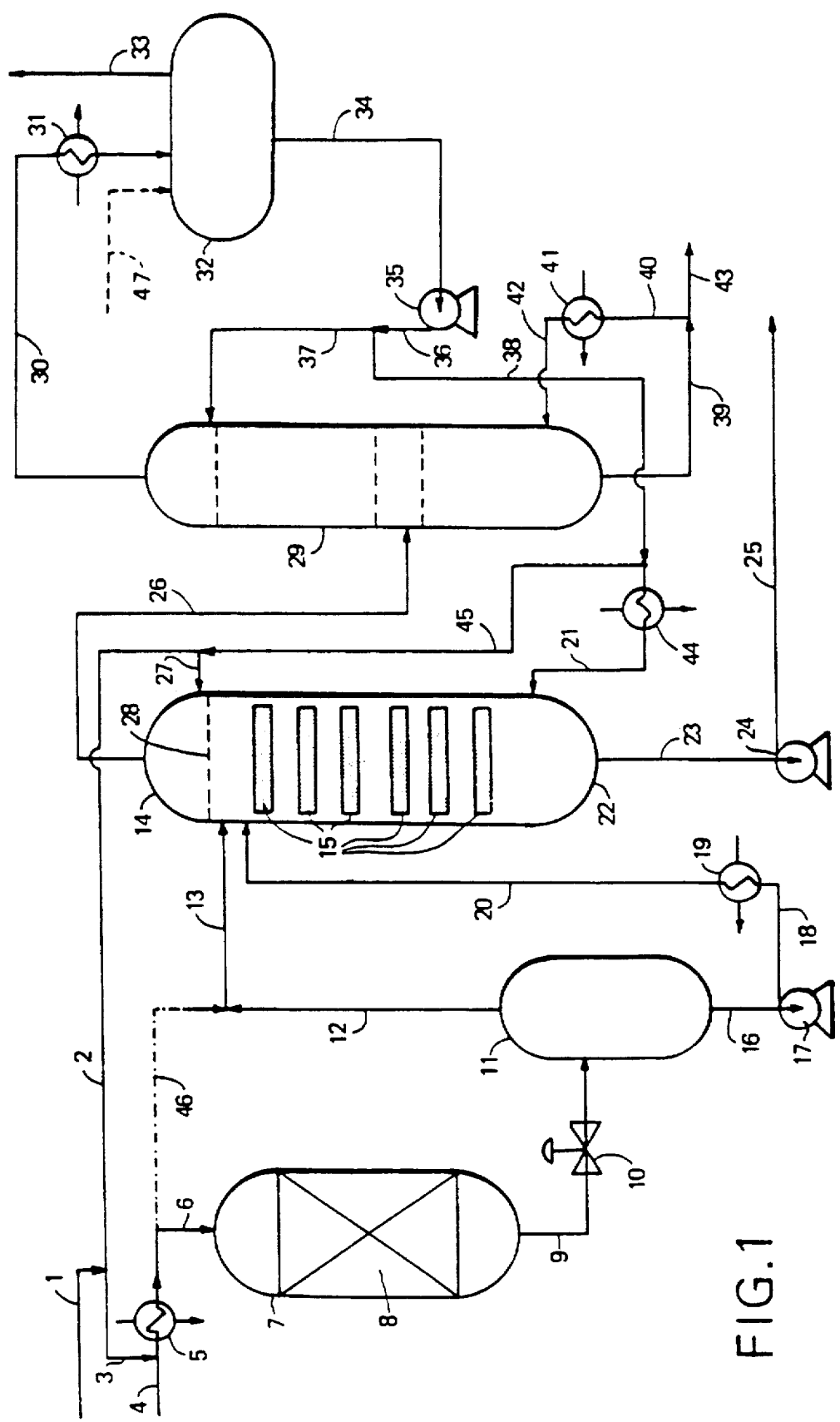
FIG. 1 is a flow diagram of a plant for the production of methyl esters of fatty acids wherein the plant is constructed in accordance with the invention.

The process of the invention utilises the vaporous stream of the more volatile of the two components, i.e. the more volatile out of the carboxylic acid component and the alcohol component, to carry away water of esterification produced in the esterification reactor but without carrying with it significant quantities of the other, i.e. the less volatile one, of the two components or of the carboxylic acid ester. For this reason it is essential that the boiling point of the vaporous mixture exiting the esterification reactor, or of the highest boiling compound present in that vaporous mixture, shall be significantly lower, at the pressure prevailing in the uppermost stage of the esterification reactor, than the boiling point at that pressure either of the less volatile one of the two components, i.e. the less volatile out of the carboxylic acid component and the alcohol component, or of the carboxylic acid ester product. By the term "significantly lower" we mean that the boiling point difference shall be at least about 20° C., and preferably at least about 25° C., at the relevant operating pressure.

As examples of monoesterification reactions that can be conducted according to the present invention there can be mentioned the production of alkyl esters of aliphatic monocarboxylic acids from alkanols and aliphatic monocarboxylic acids or anhydrides thereof. Such monocarboxylic acids may contain, for example, from about 6 to about 26 carbon atoms and may include mixtures of two or more thereof. Alkyl esters derived from alkanols containing 1 to about 10 carbon atoms are of especial importance.

Such monocarboxylic acids include fatty acids such as decanoic acid, dodecanoic acid, tetradecanoic acid, hexadecanoic,acid, octadecanoic acid, octadecenoic acid, linoleic acid, eicosanoic acid, isostearic acid and the like, as well as mixtures of two or more thereof. Mixtures of fatty acids are produced commercially by hydrolysis of naturally occurring triglycerides of vegetable origin, such as coconut oil, rape seed oil, and palm oils, and triglycerides of animal origin, such as lard, tallow and fish oils. If desired, such mixtures of acids can be subjected to distillation to remove lower boiling acids having a lower boiling point than a chosen temperature (e.g. $C_8$ to $C_{10}$ acids) and thus produce a "topped" mixture of acids, or to remove higher boiling acids having a boiling point higher than a second chosen temperature (e.g. $C_{22+}$ acids) and thus produce a "tailed" mixture of acids, or to remove both lower and higher boiling acids and thus produce a "topped and tailed" mixture of acids. Such fatty acid mixtures may also contain ethylenically unsaturated acids such as oleic acid. These fatty acid mixtures can be esterified with methanol to yield methyl fatty acid ester mixtures that can be hydrogenated to yield mixtures of alkanols, e.g. $C_8$ to $C_{20}$ alkanols (often called detergent alcohols), that are acceptable for production of detergents without prior separation of the alkanols one from another. Such hydrogenation can be conducted either in the liquid phase or in the vapour phase (in which case hydrogenation conditions are advantageously selected such that the vaporous mixture in contact with the catalyst is always above its dew point, preferably at least about 5° C. above its dew point). As examples of suitable hydrogenation catalysts there can be mentioned copper chromite and reduced copper oxide-zinc oxide hydrogenation catalysts of the type disclosed in GB-B-2116552.

Another class of carboxylic acid esters that can be produced by the process of the invention are dialkyl esters of aliphatic and cycloaliphatic $C_4$ to $C_{18}$ saturated and unsaturated dicarboxylic acids. These can be produced by reaction of alkanols with the dicarboxylic acids or anhydrides thereof, or with mixtures of the dicarboxylic acid and its anhydride. Dialkyl oxalates, dialkyl maleates, dialkyl succinates, dialkyl fumarates, dialkyl glutarates, dialkyl pimelates, and dialkyl azelaates are examples of such dicarboxylic acid esters. Other examples of such esters include dialkyl esters of tetrahydrophthalic acid. The $C_1$ to $C_{10}$ alkyl esters of such dicarboxylic acids are of particular interest. Either the free dicarboxylic acid or its anhydride (if such exists) or a mixture of dicarboxylic acids and anhydride can be used as the carboxylic acid component starting material for production of such dialkyl esters. Alkyl esters of aromatic $C_7$ to $C_{20}$ monocarboxylic acids and mixtures thereof can be made by a process of the invention. Benzoic acid and 1-naphthoic acid are examples of such acids.

Alkyl esters of aromatic $C_8$ to $C_{20}$ dicarboxylic acids can also be produced by the process of the invention from the acids, their anhydrides and mixtures thereof.

It is also possible to produce polyalkyl esters of polycarboxylic acids by the process of the invention. Such polycarboxylic acid moieties include, for example, citric acid, pyromellitic dianhydride, and the like.

Carboxylic acid esters of dihydric and polyhydric alcohols can be produced by the process of the invention. Examples of such esters include ethylene glycol diformate, ethylene glycol diacetate, propylene glycol diformate, propylene glycol diacetate, glyceryl triacetate, hexose acetates, and the acetate, propionate and n-butyrate esters of sorbitol, mannitol and xylitol, and the like.

In the practice of the invention the more volatile component of the two, i.e. the more volatile out of the carboxylic acid component and the alcohol component, will often be the alcohol component. For example methanol will be the more volatile component in the production from fatty acid mixtures obtained by the hydrolysis of triglycerides of methyl fatty acid ester mixtures for subsequent processing, for example for production of detergent alcohols by ester hydrogenation. On the other hand, in the production of the di-n-butyryl ester of ethylene glycol from n-butyric acid and ethylene glycol, for example, n-butyric acid will be the more volatile component. Similarly, in the production of propylene glycol diformate from propylene glycol and formic acid, the more volatile component will be the carboxylic acid component, i.e. formic acid.

The esterification conditions used in the column reactor will normally include use of elevated temperatures up to about 160° C. for example a temperature in the range of from about 80° C. to about 140° C. preferably in the range of from about 100° C. to about 125° C. Such operating temperatures will be determined by such factors as the thermal stability of the esterification catalyst, the kinetics of the esterification reaction and the vapour temperature of the vaporous component fed to the base of the column reactor at the relevant inlet pressure. Typical operating pressures at the vapour inlet of the column reactor range from about 0.1 bar to about 25 bar. A liquid hourly space velocity through the column reactor in the range of from about 0.1 hr$^{-1}$ to about 10 hr$^{-1}$, typically from about 0.2 hr$^{-1}$ to about 2 hr$^{-1}$, may be used.

The alcohol component or the carboxylic acid component or a mixture thereof may be supplied to an upper part of the column reactor in liquid form, in solution in recycled ester product or in solution in an inert solvent or diluent therefor. In some cases it may be desired to prereact the alcohol component and the carboxylic acid component prior to introduction to the column reactor. Such prereaction may be used, for example, in a case in which reaction between the two components can be initiated in the absence of added catalyst. The reaction of an acid anhydride, such as maleic anhydride or phthalic anhydride, with an alcohol component, such as an alkanol (e.g. methanol, ethanol or n-butanol) is an example of such a reaction, the formation of the corresponding monoester occurring under moderate conditions, e.g. 60° C. and 5 bar, without the need of any added catalyst, according to the following equation:

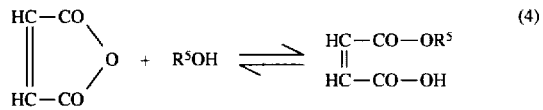

(4)

where $R^5$ is an alkyl radical, such as methyl, ethyl or n-butyl. This monoester is still a monocarboxylic acid. In addition some formation of diester will occur:

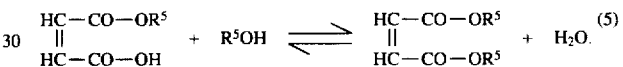

(5)

The resulting reaction mixture may contain a mixture of monoester, diester, water, and alkanol. Further alkanol can be added, if desired, to the mixture prior to introduction to the column reactor for conversion of the monoester to the diester.

In other cases, even when a monocarboxylic acid ester is the desired product, the alcohol component and the carboxylic acid component can be reacted to equilibrium in the presence of an acidic ion exchange resin containing —$SO_3H$ and/or —COOH groups prior to introduction of the resulting equilibrium mixture to the column reactor.

In the process of the invention a vaporous mixture exits the column reactor as an overhead product. Provision may be made for scrubbing such vaporous mixture with the more volatile component (usually the alcohol component) in liquid form in order to wash traces of carboxylic acid ester product and of the other component (usually the carboxylic acid component) back into the column reactor. This overhead product from the column reactor can be condensed and treated in known manner to separate its constituents, the recovered water of esterification being rejected and the more volatile component (usually the alcohol component) being recycled for re-use in as dry a form as is practicable within the relevant economic constraints. The lower the water content of the vapour that is supplied to the lowermost one of said esterification trays, the further towards 100% conversion to ester the esterification equilibrium reaction can be driven and the lower the residual acidity of the ester containing product recovered from the bottom of the column reactor will be. However, a balance may often have to be struck between the cost of providing, for example, a substantially dry alkanol for vaporisation into the column reactor, on the one hand, and the cost of providing and operating any additional downstream processing facilities that may be required to upgrade the ester product to the required quality if a less dry alkanol is used. This will vary from alkanol to alkanol and will depend upon the interaction between water and alkanol (e.g. azeotrope formation) and its effect upon alkanol/water separation. Preferably, when using an upflowing alkanol vapour in the column reactor, the water content of the alkanol vapour supplied to the reactor is less than about 5 mole %, and even more preferably is less than about 1 mole %.

The column reactor has a plurality of esterification trays. Although two or three trays may suffice in some cases, it will typically be necessary to provide at least about 5 up to about 20 or more esterification trays in the column reactor. Typically each esterification tray is designed to provide a residence time for liquid on each tray of from about 1 minute up to about 120 minutes, preferably from about 5 minutes to about 60 minutes.

The solid esterification catalyst may be a granular ion exchange resin containing —$SO_3H$ and/or —COOH groups. Macroreticular resins of this type are preferred. Examples of suitable resins are those sold under the trade marks "Amberlyst", "Dowex", "Dow" and "Purolite" such as Amberlyst 13, Amberlyst 66, Dow C351 and Purolite C150.

Different solid esterification catalysts may be used on different trays of the column reactor. Moreover different concentrations of solid esterification catalyst can be used on different trays.

The charge of solid particulate or granular esterification catalyst on each tray is typically sufficient to provide a catalyst:liquid ratio on that tray corresponding to a resin concentration of at least 0.2% w/v, for example a resin concentration in the range of from about 2% w/v to about 20% w/v, preferably 5% w/v to 10% w/v, calculated as dry resin. Sufficient catalyst should be used to enable equilibrium or near equilibrium conditions to be established on the tray within the selected residence time at the relevant operating conditions. On the other hand not so much catalyst should be used on each tray that it becomes difficult to maintain the catalyst in suspension in the liquid on the tray by the agitation produced by the upflowing vapour entering the tray from below. For a typical resin catalyst a resin concentration in the range of from about 2% v/v to about 20% v/v, preferably 5% v/v to 10% v/v may be used.

The particle size of the catalyst should be large enough to facilitate retention of the catalyst on each tray by means of a screen or similar device. However, as the larger the catalyst particle size is the more difficult it is to maintain in suspension and the lower the geometrical surface area per gram, it is expedient to use not too large a catalyst particle size. A suitable catalyst particle size is in the range of from about 0.1 mm to about 5 mm.

One or more wash trays may be provided above the esterification trays in order to prevent loss of product, solvent and/or reagents from the column reactor.

In the column reactor the vapour upcomer means associated with each esterification tray may comprise a sparger positioned so that, in operation, it will lie below the surface of the mixture of liquid and solid esterification catalyst on that tray and so that vapour bubbles emerging therefrom will agitate said mixture of liquid and solid particulate catalyst. The sparger may be a ring sparget. At least one baffle means may be mounted in the vicinity of the sparger to enhance the mixing action thereof. For small scale operation a sparger on the axis of the column reactor under a cylindrical baffle can be used.

In one embodiment the sparger is a ring sparger and inner and outer annular baffle means are positioned in the vicinity of the sparger and define an upflow zone in the region of upflowing vapour bubbles and adjacent downflow zones within and outside the upflow zone.

It is important to avoid stagnant zones where solid esterification catalyst can settle out because this can lead to excessive formation of by-products or to occurrence of hot spots. Although mechanical stirrers can be provided on each tray to maintain the catalyst particles suspended in liquid, this adds somewhat to the complexity of the reactor. It is possible, however, by suitable design of the sparger and tray to ensure that the upflowing vapour provides sufficient agitation in passage through the liquid on the tray to maintain the catalyst particles in suspension. To achieve this end it is convenient if at least a part of the floor of one or more (and preferably all) of the esterification trays slopes towards a zone where there is turbulence caused by the upflowing vapour such as is to be found under the sparger. The angle of slope is preferably selected so as to be equal to or greater than the angle of repose of the solid particulate esterification catalyst under the liquid in the esterification tray. The adoption of such a slope will tend to ensure that all of the catalyst is in dynamic contact with the liquid during operation and that no stagnant zones of catalyst are formed. Such stagnant zones are undesirable because they can enable undesirable side reactions or even thermal runaways to occur in certain instances.

In a preferred apparatus the vapour upcomer means of one or more (and preferably all) of the esterification trays is or are provided with a liquid suckback preventer means.

A screen means may be provided on at least one esterification tray to hinder loss of solid esterification catalyst from that esterification tray via its associated downcomer means. In this way downward flow of the solid catalyst from one esterification tray to the next lower one can be substantially prevented.

Means may be provided for withdrawing resin from, or adding resin to, one or more of the trays during operation of the column reactor. For example, a conduit having a down turned open end can extend into the interior of a respective tray with its open lower end positioned at a low point within the tray. By this means a slurry of catalyst and liquid can be withdrawn in controlled manner from the tray intermittently or continuously, as desired, or further catalyst can be introduced in slurry form to the trays, as desired. Catalyst withdrawn from a given tray can be re-introduced into the column reactor, either into the same tray or to a lower or higher one, possibly after being given a regeneration treatment.

In order that the invention may be clearly understood and readily carried into effect three preferred forms of plant for continuous production of esters, and corresponding preferred processes for use in connection therewith, will now be described, by way of example only, with reference to the accompanying drawings, in which:

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Referring to FIG. 1 of the drawings, methanol is supplied to the plant in line 1 and is admixed with recycled methanol in line 2 to form a methanol feed to the plant in line 3. A fatty acid mixture, for example a mixture of fatty acids obtained by hydrolysis of a naturally occurring triglyceride, e.g. coconut oil, followed by "topping and tailing", is fed in line 4 and mixed with the methanol feed from line 3 before flowing to a heat exchanger 5, in which its temperature is raised to 110° C. The heated acid/methanol mixture flows on in line 6 into primary esterification reactor 7, which contains a charge 8 of an ion exchange resin containing sulphonic acid and/or carboxylic acid groups, such as Amberlyst 13. (The word "Amberlyst" is a trade mark). The pressure in reactor 7 is 5 bar.

Figure 3:
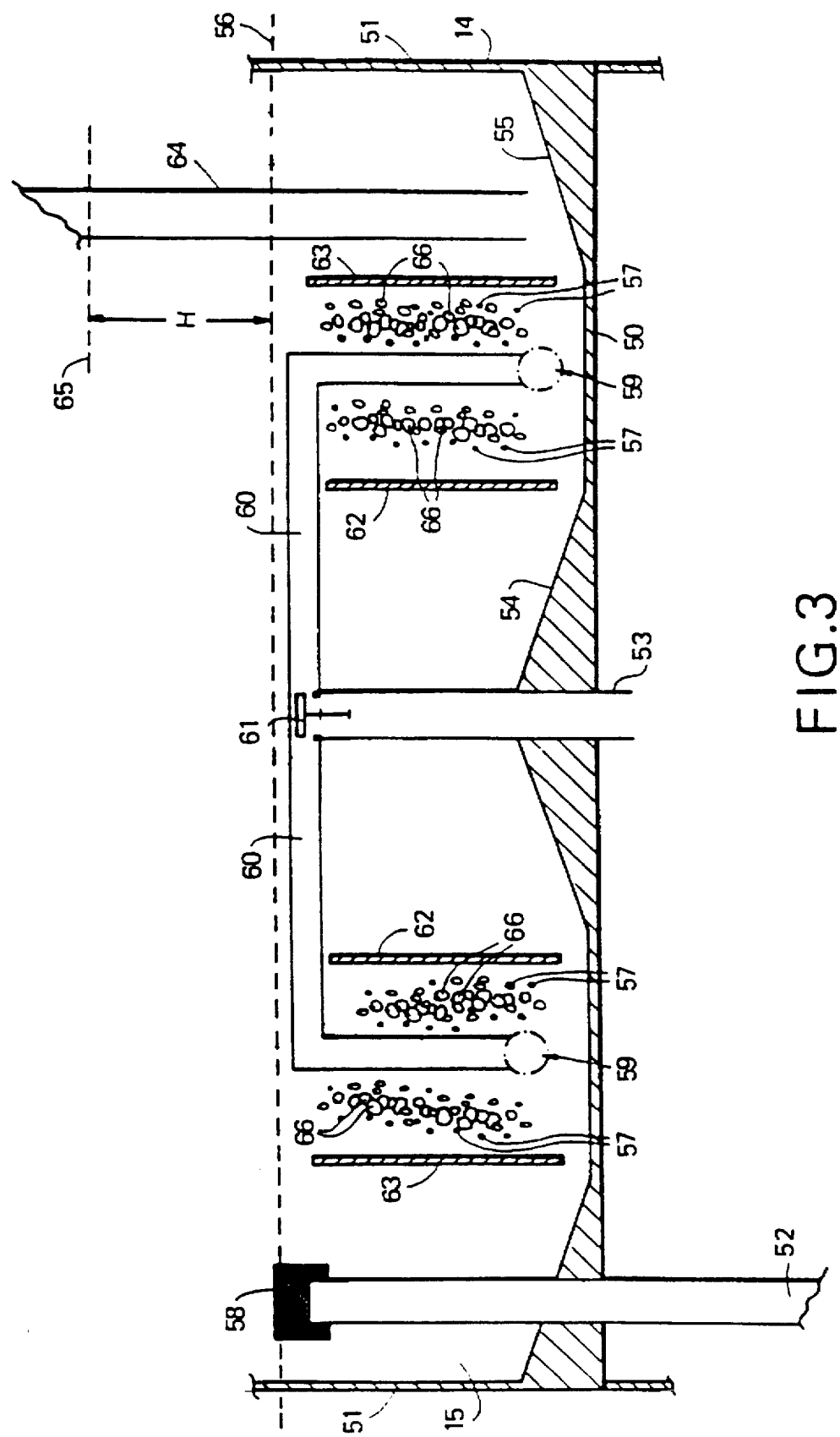
FIG. 3 illustrates an esterification tray in one embodiment of the invention.
Figure 4:
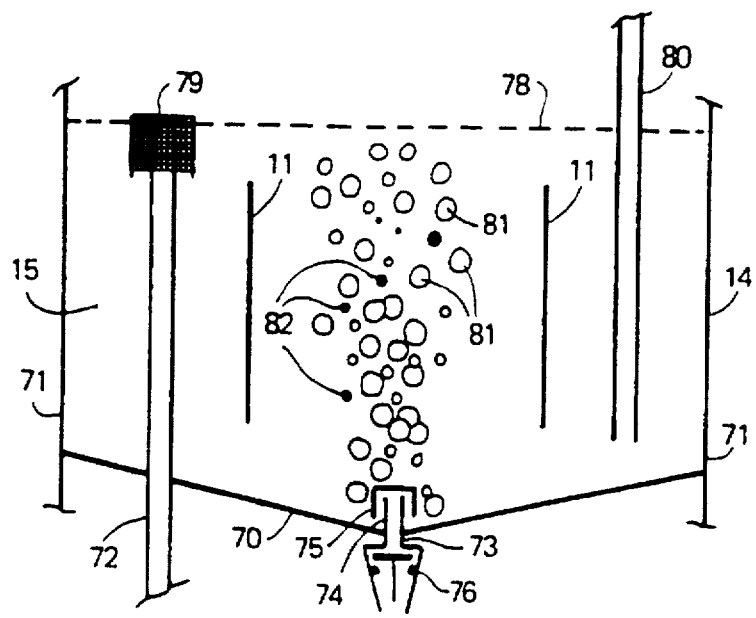
FIG. 4 illustrates an esterification tray in another embodiment of the invention.

In reactor 7 part of the acid mixture is esterified by reaction with methanol to yield a corresponding mixture of methyl fatty acid esters. There exits from reactor 7 in line 9 a mixture of methyl esters, unreacted fatty acid, water produced by esterification and unreacted methanol. This mixture passes through a pressure let down valve 10 into a vapour/liquid separator 11. A vapour phase comprising methanol and water is fed at 1.3 bar by way of lines 12 and 13 to an upper part of an esterification reactor 14. Reactor 14 is provided with a number of esterification trays 15; two possible forms of esterification tray 15 are illustrated in FIGS. 3 and 4 and will be described in greater detail below. In the plant of FIG. 1 there are six trays 15; however, a greater or lesser number of such trays (e.g. any number from 3 to 5 or 7 to 20) may be provided, depending upon the nature of the fatty acid and the reaction conditions selected.

The liquid phase from vapour/liquid separator 11 is fed by way of line 16, pump 17 and line 18 to heat exchanger 19, in which it is heated by steam to a temperature of up to 150° C., e.g. 120° C., and then by means of line 20 to reactor 14 at a point below the entry point of line 13.

In reactor 14 the downflowing unreacted fatty acids in the mixture in line 20 pass downwardly from each esterification tray 15 to the next lower tray 15 against an upflowing current of vapour comprising methanol and water of esterification, i.e. water produced as a result of the esterification reaction. Dry methanol vapour is supplied to reactor 14 in line 21. Each esterification tray 15 holds a charge of an acidic ion exchange resin, such as a resin containing sulphonic acid groups. Amberlyst 13 is a suitable resin. (Amberlyst is a trade mark). In passage down column 14 any unreacted free acid encounters progressively drier methanol vapour on each tray 15. By designing each tray 15 to provide an appropriate liquid hold up, it is possible to regulate the residence time on each tray 15. By selecting a suitable number of trays 15 it is further possible to design reactor 14 so that essentially no free fatty acid remains in the liquid passing downwards from the bottom tray 15 into the sump 22 of reactor 14. Methyl ester product (i.e. a mixture of methanol and methyl esters derived from the mixed fatty acids supplied in line 4) is removed from sump 22 in line 23 and pumped onward by pump 24 via line 25 for further treatment or to a product refining facility or to storage.

A mixture of methanol vapour and the water released in the esterification reaction is recovered overhead from reactor 14 in line 26. Liquid methanol is supplied in line 27 to an upper part of reactor 14 above the point of connection of line 13 to provide liquid methanol on wash tray 28.

The vapour in line 26 is fed to a methanol/water separation column 29 which is operated at 1.3 bar and at a head temperature of 70° C. Dry methanol vapour is recovered overhead in line 30 and is condensed in condenser 31. The resulting condensate is collected in drum 32 which is vented as indicated at 33. Dimethyl ether produced as byproduct is vented in line 33. Methanol which would otherwise be lost along with the dimethyl ether can be recovered by providing a chilled condenser (not shown) in line 31. Part of the condensed methanol is recycled to column 29 from drum 32 as a reflux stream in line 34 by means of pump 35 and lines 36 and 37. The remainder is pumped back for re-use in line 38.

The sump product from column 29 consists essentially of water. This is withdrawn in line 39. Part is recycled to column 29 by way of line 40, steam heated reboiler 41 and line 42; the remainder is passed on in line 43 for effluent treatment.

Some of the dry methanol in line 38 is passed through vaporiser 44 to provide the stream of dry methanol vapour in line 21. The rest flows on in line 45 to provide the recycle streams in lines 2 and 27.

In a modification of the plant of FIG. 1 reactor 7 and vapour/liquid separator 11 are omitted and the mixture of fatty acids and methanol is fed by way of line 46 to line 13.

In a further modification of the plant of FIG. 1 lines 1 to 3 and items 6 to 12 and 16 to 20 are omitted. Thus liquid fatty acid or fatty acid mixture is the sole liquid feed to reactor 14 and is supplied by way of lines 4, 46 and 13. Make up methanol for the plant can be supplied through line 47 to reflux drum 32.

Figure 2:
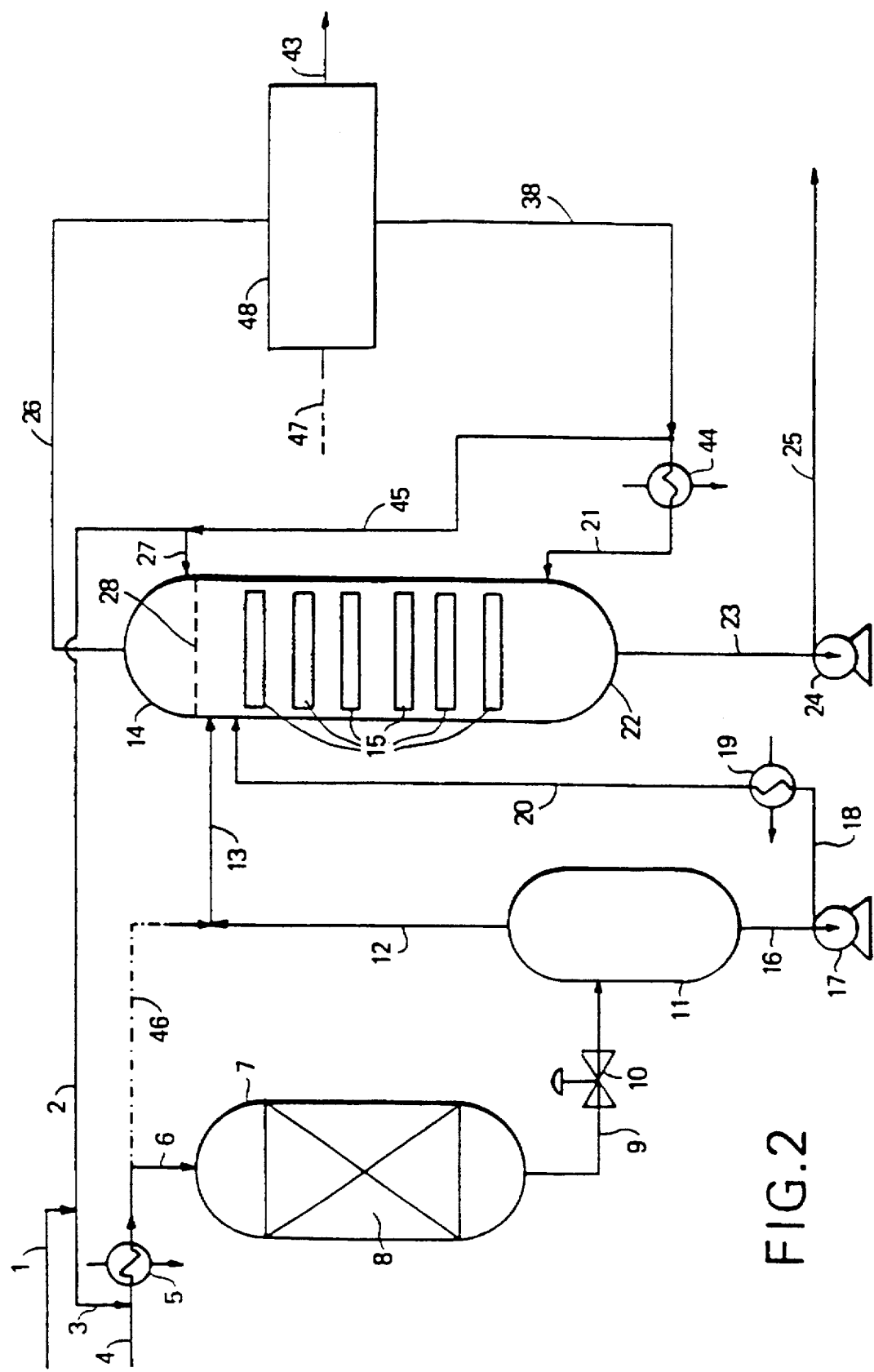
FIG. 2 is a flow diagram of a plant for the production of a carboxylic acid ester which has a significantly higher boiling point than the alcohol from which the alcohol moiety is derived, than water, or than any alcohol/water azeotrope formed.

FIG. 2 illustrates an alternative form of plant suitable for production of mono-, di- and polycarboxylic acid esters which have a significantly higher boiling point than that of the alcohol used and of any water/alcohol azeotrope that may be formed.

In the plant of FIG. 2 the same reference numerals are used to indicate like parts to those present in the plant of FIG. 1, except that line 1 is used for supply, not of methanol, but of a higher alcohol such as ethanol or a higher alkanol containing up to 10 carbon atoms. The product in line 25 is thus an ethyl or higher ester of a mono-, di- or polycarboxylic acid. Reference numeral 48 indicates any suitable alkanol/water separation plant.

Similar modifications to the plant of FIG. 2 can be made to those described above, i.e. omission of items 1 to 3, 6 to 12 and 16 to 20 to permit supply of liquid fatty acid or fatty acid mixture as the sole liquid feed to reactor 14.

FIG. 3 illustrates one form of construction of a tray 15 of reactor 14 of the plants of FIGS. 1 and 2. A horizontal diaphragm or partition 50 extends within wall 51 of reactor 14 and closes off the cross section of reactor 14 completely except for a downcomer 52 for liquid and a vapour upcomer 53. Partition 50 has an axial frusto-conical part 54 surrounding vapour upcomer 53 and an annular sloping portion 55 adjacent wall 51. Tray 15 can thus retain a volume of liquid whose surface is indicated at 56 and whose volume is determined by the height of the overflow level of downcomer 52 above the partition 50. Each tray 15 also supports a charge of an acidic ion exchange resin containing —$SO_3H$ groups, such as Amberlyst 13, whose particles are indicated diagrammatically at 57. Such ion exchange particles are kept in suspension in the liquid on tray 15 as a result of agitation caused by the upcoming vapour as will be described below. To prevent escape of ion exchange particles 57 with the liquid overflowing down downcomer 52 the top of downcomer 52 is provided with a screen 58. The slope of frusto-conical part 54 and of sloping portion 55 is equal to or greater than the angle of repose of the Amberlyst 13 or other solid particulate esterification catalyst under the liquid on esterification tray 15.

Vapour upcomer 53 conducts upcoming vapour to a circular sparger 59, which surrounds frusto-conical part 54, by way of spider tubes 60. Suckback of liquid down upcomer 53 is prevented by means of an anti-suckback valve 61.

Annular draught shrouds or baffles 62 and 63 are positioned within the body of liquid on tray 15, one inside and one outside circular sparger 59 to promote agitation of the liquid/resin suspension by the upcoming vapour. The vertical extent of shrouds 62 and 63 is not critical but should generally be between one third and three quarters of the vertical height between diaphragm 50 and liquid surface 56. It is preferred that shrouds 62 and 63 should be placed in a symmetrical or near symmetrical vertical position. In the annular zone between shrouds 62 and 63 the liquid flow is generally upward whilst inside shroud 62 and outside shroud 63 the general direction of liquid flow is downward. Preferably the area of the annular zone between shrouds 62 and 63 approximately equals the sum of the areas inside shroud 62 and outside shroud 63.

Reference numeral 64 indicates a downcomer from the next tray above the one illustrated in FIG. 3. The liquid level in downcomer 64 is indicated at 65, the height H of this liquid level above liquid level 56 on tray 15 being fixed by the liquid level on the tray which feeds downcomer 64 (i.e. the tray above the illustrated tray 15) plus the pressure drop through the sparger 59 on that tray (i.e. the one above the illustrated tray 15) and the frictional pressure drop.

In operation of reactor 14 a mono, di- or polycarboxylic acid or mixture of acids is typically passed downwards in liquid form in countercurrent to an upflowing vaporous stream of alcohol. Each tray 15 acts as an esterification zone containing a respective charge of esterification catalyst which catalyses the esterification reaction and the release of water of esterification. Under the countercurrent conditions prevailing in the reactor 14 such water of esterification is vaporised and carried upwards through reactor 14 with the upflowing alcohol vapour. The liquid passes downwards from one tray 15 to the next downward tray 15 and the free acid concentration in the liquid on each tray 15 is lower than the corresponding acid concentration in the liquid on the next higher tray 15. In addition the liquid encounters drier and drier alcohol vapour on each tray 15 as it passes down through reactor 14. In this way the equilibrium of the esterification reaction is pushed further towards ester formation, the reverse hydrolysis reaction being effectively suppressed because the water concentration in the liquid on the trays 15 decreases from tray to tray in the downward direction.

By selecting a suitable number of trays 15 in column 14 and designing each tray 15 to provide a sufficient liquid hold up to provide the requisite residence time on each tray it is possible to design reactor 14 so that the product in line 25 contains less than about 1 mole % of carboxylic acid, together with fatty acid esters and alcohol as its principal components. By providing an adequate upflow rate for alcohol vapour the agitation caused by the vapour bubbles 66 emerging from circular sparger 59, coupled with the liquid circulation induced by the presence of draught shrouds 62 and 63, can suffice to maintain the acidic ion exchange resin particles sufficiently in suspension for esterification to proceed successfully. The surfaces of sections 54 and 55 slope towards the zone under the sparger 59 and ensure that there are no stagnant zones where significant quantities of resin can settle out of suspension. (It will be appreciated that, although FIG. 3 only shows resin particles 57 in suspension in the zone between draught shrouds 62 and 63, they would in practice be present in suspension in the liquid phase outside this zone). If necessary, the volume of the upflowing vapour can be boosted by inert gas or by other vaporisable inert material, conveniently an inert material that is a byproduct of the process. For example, it is often found that an ether is found amongst the byproducts, as acidic catalysts can promote formation of an ether from the alcohol used. Thus dimethyl ether is a potential byproduct if methanol is used as the alcohol, whilst diethyl ether can be formed in reactor 14 if ethanol is the alcohol used; either material can be used, if necessary, to boost vapour upflow to provide additional agitation on trays 15 or to provide additional vapour to carry away water of esterification.

In FIG. 4 there is illustrated an alternative design of esterification tray 15 suitable for use in a relatively small scale reactor 14. In this case a frusto-conical partition or diaphragm 70 extends within wall 71 of reactor 14 and closes off the cross section of reactor 14 completely except for a downcomer 72 for liquid and a vapour upcomer 73. The slope of frusto-conical diaphragm 70 is equal to or greater than the angle of repose of the solid particulate catalyst under the liquid present on tray 15. The vapour upcomer 73 includes an axial sparger 74 provided with a bubble cap 75 and is fitted with an anti-suckback valve 76. Optionally bubble cap 75 can be surrounded by a mesh screen (not shown) to prevent ingress of catalyst particles interfering with the operation of valve 76. A cylindrical baffle 77 surrounds sparger 74 symmetrically and is positioned beneath the liquid level 78, the height of which is determined by the height of the upper end of downcomer 72. A screen 79 is fitted to the top of downcomer 72 to retain solid esterification catalyst, e.g. Amberlyst 13, on tray 15. Reference numeral 80 indicates the downcomer from the next higher esterification tray 15 (not illustrated). In a similar manner to that described in relation to FIG. 3 the bubbles 81 of vapour agitate the liquid on tray 15 and maintain particles 82 of catalyst in suspension. Baffle 77 defines an upflow zone within baffle 77 and a downflow zone outside baffle 77. Preferably the areas of the two zones are substantially equal. This design ensures that, so far as is possible, no stagnant zones where catalyst particles can sediment are formed.

If desired the feed line 20 or 13 in the plants of FIGS. 1 and 2 can be arranged to discharge onto a tray, similar to tray 15 of FIG. 3 or FIG. 4, which does not hold a charge of ion exchange resin. One or more alkanol wash trays may be provided above the connection of feed line 20 or 13 so that the vapours are scrubbed with a minor amount of liquid alkanol before exiting reactor 14 in line 26 so as to limit the amount of acid or ester to traces therein.

Figure 5:
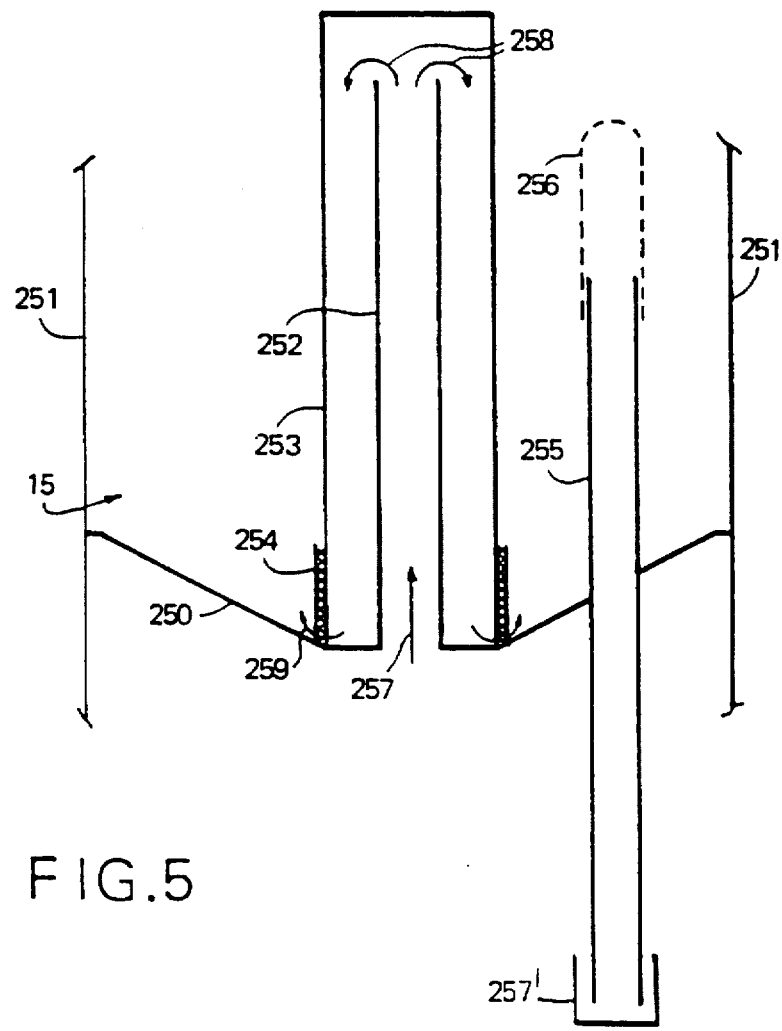
FIG. 5 illustrates an esterification tray in yet another embodiment of the invention.

FIG. 5 illustrates a further design of esterification tray 15 suitable for use in a laboratory scale reactor 14 or in a commercial scale reactor 14. This comprises a generally frusto-conical partition or diaphragm 250 which extends within wall 251 of reactor 14. The slope of the upper surface of diaphragm 250 is greater than the angle of repose of the solid particulate catalyst. A vapour upcomer 252 is fitted with a cap 253 with a dependent skirt of mesh 254. Downcomer 255 is fitted with a mesh cap 256 and with a seal bucket 257. The upper end of downcomer 255 is positioned so as to provide a suitable retention volume for liquid on tray 15 whilst mesh skirt 254 and mesh cap 256 retain the charge of resin particles on diaphragm 250. Methanol vapour flows up upcomer 252 as indicated by arrow 257, through the space between upcomer 252 and cap 253 as indicated by arrows 258, and through skirt 254 as indicated by arrows 259, and carries with it water vapour resulting from water of esterification formed in a lower tray or trays.

Figure 6:
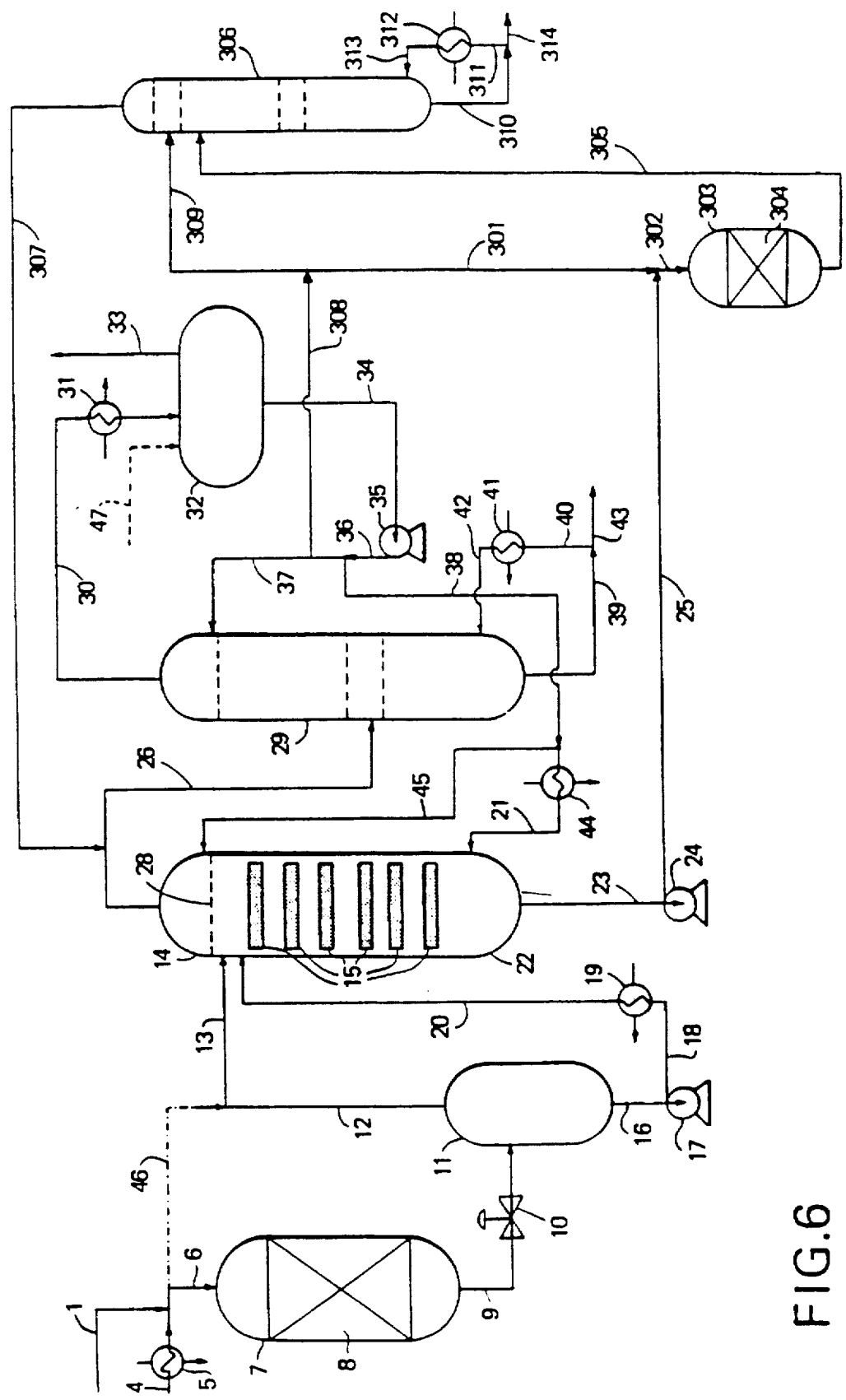
FIG. 6 is a flow diagram of the plant illustrated in FIG. 1 except that there is no feed line 2 for recycle methanol.

The plant of FIG. 6 is generally similar to that of FIG. 1 and like reference numerals have been used in both Figures to indicate like parts. The feed acid in line 4 is typically an unsaturated fatty acid, such as oleic acid.

In the plant of FIG. 6 line 2 is omitted so that there is no recycle of methanol for admixture with the feed methanol in line 1. Hence all of the methanol in line 45 is supplied to wash tray 28.

As the number of theoretical stages in column 14 does not necessarily correspond to the number of trays 15 fitted in column 14, and the number of such theoretical stages may vary, for a particular column, for different feed acids supplied in line 4, the acid content of the methyl ester product in line 23 may vary if the nature of the feed acid in line 4 is changed.

As already mentioned a by-product of ester formation in the column is often a dialkyl ether. The yield of such dialkyl ether by-product is found to be dependent upon the temperature of operation of the reactor 14. Hence by minimising the temperature of operation of column reactor 14 the yield of by-product ether can be minimised. However, a corollary of this is that a lower conversion of acid to ester is obtained at lower operating temperatures. In this case it is possible to optimise the conversion to ester by admixing the ester-containing product, which contains perhaps about 97 mole % to about 99 mole % of ester with the balance being acidic materials, with further alkanol (e.g. methanol) and passing the resulting mixture containing, for example, a 2:1 to 4:1, e.g. 3:1, alkanol:ester molar mixture through a polishing reactor having a fixed bed of a solid esterification catalyst, such as Amberlyst 13, which can be operated at a lower temperature than the column reactor. In this way extremely high overall conversion to ester can be achieved. Such a modified form of plant is illustrated in FIG. 6.

In the plant of FIG. 6 there are six esterification trays 15 and the methyl ester product in line 23 still contains a minor amount of oleic acid. Typically the methyl oleate:oleic acid molar ratio is in the region of 97:3. This mixture is admixed with further methanol supplied from line 301 to form a mixture having a molar ratio of methanol:methyl oleate:oleic acid of 3:0.97:0.03. This mixture is supplied in line 302 at a temperature of 60° C. and at a liquid hourly space velocity of 1 hr$^{-1}$ to a further esterification reactor 303 containing a fixed bed 304 of an acidic ion exchange resin, such as Amberlyst 13. The resulting mixture flows on in line 305 to a further distillation column 306. Methanol vapour passes overhead via line 307 to column 29 via line 26. Liquid methanol to form a reflux stream and the stream in line 301 is pumped from condensate drum 32 by pump 35 through line 308. The reflux stream flows on in line 309 to column 306. The bottom product from column 306 in line 310 comprises essentially pure methyl oleate (of purity at least 99.5 mole %). Part is recycled to column 306 by way of line 311 via column reboiler 312 and line 313, whilst the remainder is passed to storage or onward for further treatment in line 314.

The plants of FIGS. 1 and 2 and the trays 15 illustrated in FIGS. 3 and 4 have been described in the context of acid containing liquid phase downflow and upcoming vaporous alcohol flow. If the acid used is more volatile than the alcohol component, then the directions in which the acid and alcohol components flow can be reversed, so that the alcohol is in liquid phase and flows down from one tray 15 to the next downward tray 15 through reactor 14 whilst acid vapour passes upwardly in countercurrent thereto.

The invention is further illustrated in the following Examples.

EXAMPLE 1

A laboratory scale column reactor with an internal diameter of 76.2 mm made of glass QVF components and having ten trays one above another was used. Each tray had the form illustrated in FIG. 5. The column reactor was lagged and wound with external electrical heating tapes. Each tray had its own temperature control system. The top tray contained no resin and acted as a liquid scrubbing tray to limit losses of the acid feed or of the ester product. The second tray from the top also contained no resin and was supplied with the acid feed. The remaining eight trays each held a charge of Amberlyst 16 ion exchange resin which had been sieved to remove beads with a particle size less than 355 µm and then washed extensively with methanol and then dried at 105° C. to constant weight. The mesh size of the stainless steel mesh of skirt 254 and of cap 256 was 300 µm. Dry methanol was vaporised by passage through a coil immersed in an oil bath at 150° C. and the resulting vapour was fed to the bottom of the column reactor below the lowermost tray. Each tray held about 240 ml of liquid. The resin charge on each tray corresponded to 14% by weight calculated as dry resin based on the liquid charge on each tray. The overhead vapour from the column reactor, which consisted of unreacted methanol, water which is produced in the course of esterification, and a minor amount of by-product dimethyl ether, was condensed. A constant head overflow device was used to control the rate of removal of product esters from the column reactor.

At start up the column reactor was charged with resin and with methyl laurate. When the methanol flow and the temperatures of the various trays had stabilised a feed of 50 mole % methyl laurate, 40 mole % lauric acid, and 10 mole % myristic acid was supplied to the column. This feed mixture was similar to the mixture in line 20 of FIG. 1 when that plant is supplied in line 4 with a mixture of lauric acid and myristic acid. The level of $C_{14}$ ester in the bottoms product from the column reactor was monitored until an equilibrium level was attained. The liquid on each tray was analysed. The results are summarised in Table I below; the trays are numbered from 1 to 10, tray No. 1 being the top tray and tray No. 10 being the bottom tray.

TABLE I

| MeOH:Acid mole ratio | 5:1 | 3.6:1 | 3:1 |
|---|---|---|---|
| Residence time (hours) | 2.6 | 2.2 | 2.0 |
| Tray No. | Mole % Conversion | | |
| 5 | 98.32 | 96.53 | 96.16 |
| 6 | 99.39 | 98.76 | 97.05 |
| 7 | 99.62 | 99.15 | 97.25 |
| 8 | 99.87 | 99.45 | 98.74 |
| 9 | 99.93 | 99.75 | 99.48 |
| 10 | ND | 99.81 | 99.76 |
| DME make | 3.0 | 2.7 | 1.5 |

In Table I and in the following Tables "N.D" means "not determined", whilst "DME" means "dimethyl ether", the "DME make" being expressed as a percentage by weight of the acid feed.

EXAMPLE 2

The same column reactor as was used in Example 1 was fed with a mixture of natural straight chain fatty acids of the following composition:

| Component | % by weight |
|---|---|
| $C_8$ acid | 5.10 |
| $C_{10}$ acid | 4.62 |
| $C_{12}$ acid | 40.64 |
| $C_{14}$ acid | 14.12 |
| $C_{16}$ acid | 9.57 |

-continued

| Component | % by weight |
|---|---|
| $C_{18}$ acids | 25.01 |
| Unknowns | 0.77 |
| $H_2O$ | 0.17 |

The results are summarised in Table II.

TABLE II

| MeOH:Acid mole ratio | 2.7:1 | 3.8:1 | 4.2:1 | 4.1:1 | 4.7:1 | 6.7:1 |
|---|---|---|---|---|---|---|
| Residence Time (hours) | 1.9 | 3.3 | 3.6 | 3.5 | 4.6 | 4.7 |

| Tray No | Mole % Conversion | | | | | |
|---|---|---|---|---|---|---|
| 5 | 61.22 | 66.54 | 68.89 | 68.01 | 69.02 | 79.82 |
| 6 | ND | ND | ND | ND | ND | ND |
| 7 | 86.20 | 89.74 | 91.78 | 90.16 | 91.78 | 92.38 |
| 8 | 92.50 | 94.62 | 96.14 | 95.29 | 96.22 | 98.07 |
| 9 | 95.28 | 97.46 | 98.15 | 97.68 | 98.11 | 99.20 |
| 10 | 97.53 | 98.77 | 99.12 | 98.90 | 99.30 | 99.64 |
| DME Make | 2.0 | 2.8 | 2.5 | 2.7 | 2.7 | 2.8 |
| Average Temperature (°C.) | 112 | 107 | 104 | 111 | 112 | 113 |

EXAMPLE 3

The procedure of Example 2 was repeated using a 51.6:48.4 acid:ester mole ratio feed mixture. Such a mixture corresponded to a typical feed mixture in line 20 of FIG. 1. The acids used were a mixture of natural straight chain fatty acids comprising 65% by weight $C_{12}$ acid, 25% by weight $C_{14}$ acid, and 10% by weight $C_{16}$ acid. The results are shown in Table III below. In this Example the amounts of resin on a dry basis used on each tray corresponded to 10% by weight based upon the liquid retained for each of trays Nos. 3 to 7 and to 5% by weight on the same basis for trays Nos. 8 to 10.

TABLE III

| MeOH:acid mole ratio | 3:1 | 2:1 |
|---|---|---|
| Residence time (hours) | 2.5 | 2.5 |

| Tray No | Mole % Conversion | |
|---|---|---|
| 3 | 70.08 | 67.10 |
| 4 | 83.10 | 79.21 |
| 5 | 91.59 | 88.48 |
| 6 | 96.4 | 94.46 |
| 7 | 98.55 | 97.39 |
| 8 | 99.13 | 98.24 |
| 9 | 99.49 | 98.87 |
| 10 | 99.68 | 99.27 |
| DME Make | 2.1 | 1.3 |
| Average temperature (°C.) | 110 | 107 |

EXAMPLE 4

The column reactor of Example 1 was used to investigate the esterification of monoethyl maleate (MEM) with ethanol (EtOH) to form diethyl maleate (DEM). The resin loadings of the trays were the same as in Example 3. The acid feed to tray No. 2 had the following composition in mole %: $H_2O$ 25.9; EtOH 20.3; DEM 10.4; diethyl fumarate (DEF) <0.1; MEM 39.4; monoethyl fumarate (MEF) 0.1; maleic acid (MAC) 3.9; fumaric acid (FAC) <0.1; diethyl ethoxysuccinate (EDES) <0.1. A wet ethanol replaced the dry methanol used in Examples 1 to 3; this had the following composition in mole %: EtOH 84.2; $H_2O$ 15.8. The residence time in the column reactor was approximately 2.7 hours. The feed rates were 680 g/hr acid feed and 390 g/hr EtOH. The results are shown in Table IV.

TABLE IV

| Tray No. | Liquid Composition, mole % | | | | | | | | | Temp. (°C.) | Mole % conv. |
|---|---|---|---|---|---|---|---|---|---|---|---|
| | $H_2O$ | EtOH | DEM | DEF | MEM | MEF | MAC | FAC | EDES | | |
| 3 | 17.1 | 13.7 | 27.9 | 0.4 | 35.1 | 0.9 | 4.6 | 0.1 | <0.1 | 119 | 41.0 |
| 4 | 16.7 | 18.9 | 33.4 | 0.5 | 26.8 | 0.7 | 2.9 | 0.1 | <0.1 | 113 | 52.7 |
| 5 | 15.4 | 28.0 | 34.0 | 0.6 | 20.0 | 0.5 | 1.5 | <0.1 | <0.1 | 110 | 61.0 |
| 6 | 11.9 | 28.2 | 40.8 | 0.7 | 16.9 | 0.4 | 1.1 | <0.1 | <0.1 | 106 | 69.1 |
| 7 | 9.2 | 25.0 | 49.0 | 0.8 | 14.8 | 0.4 | 0.8 | <0.1 | <0.1 | 107 | 75.7 |
| 8 | 7.8 | 26.4 | 51.1 | 0.8 | 12.9 | 0.4 | 0.6 | <0.1 | <0.1 | 108 | 79.0 |
| 9 | 6.6 | 22.6 | 56.5 | 0.9 | 12.4 | 0.3 | 0.5 | <0.1 | <0.1 | 110 | 81.3 |
| 10 | 6.0 | 30.5 | 52.4 | 0.9 | 9.5 | 0.3 | 0.3 | <0.1 | <0.1 | 103 | 84.0 |

In this Example diethyl ether was a by-product; the amount of diethyl ether formed corresponded to approximately 16 g per kg of monoethyl maleate.

EXAMPLE 5

The procedure of Example 4 was repeated using the same feed mixture but with a residence time in the reactor of approximately 2.1 hours. The acid feed rate was 840 g/hr and the ethanol feed rate was 475 g/hr. The results are summarised in Table V.

TABLE V

| Tray No. | Liquid Composition, mol % | | | | | | | | | Temp. (°C.) | Mole % conv. |
|---|---|---|---|---|---|---|---|---|---|---|---|
| | H₂O | EtOH | DEM | DEF | MEM | MEF | MAC | FAC | EDES | | |
| 3 | 21.7 | 15.5 | 21.2 | 0.2 | 36.3 | 0.6 | 4.5 | <0.1 | <0.1 | 115 | 34.1 |
| 4 | 18.2 | 16.4 | 29.7 | 0.3 | 31.3 | 0.6 | 3.5 | <0.1 | <0.1 | 116 | 45.9 |
| 5 | 15.1 | 19.7 | 36.1 | 0.4 | 25.7 | 0.5 | 2.4 | <0.1 | <0.1 | 114 | 56.1 |
| 6 | 11.4 | 22.8 | 42.6 | 0.5 | 20.6 | 0.5 | 1.5 | <0.1 | <0.1 | 109 | 65.6 |
| 7 | 10.1 | 25.2 | 46.5 | 0.6 | 16.2 | 0.4 | 0.9 | <0.1 | <0.1 | 108 | 73.4 |
| 8 | 7.7 | 25.1 | 50.1 | 0.6 | 15.4 | 0.3 | 0.8 | <0.1 | <0.1 | 108 | 75.5 |
| 9 | 6.7 | 23.1 | 54.8 | 0.7 | 13.9 | 0.3 | 0.6 | <0.1 | <0.1 | 110 | 78.9 |
| 10 | 5.6 | 26.1 | 54.8 | 0.7 | 11.8 | 0.3 | 0.6 | <0.1 | <0.1 | 107 | 81.7 |

In this Example diethyl ether was a by-product; the amount of diethyl ether formed corresponded to approximately 11 g per kg of monoethyl maleate.

Examples 4 and 5 demonstrate the advantage of using the column reactor which enables mole % conversions of 84.0 and 81.7 to be achieved respectively using an alcohol:acid molar ratio of approximately 2:1. Using a fixed bed reactor it could be shown that the maximum mole % conversion would be approximately 72%, but it would then be necessary to use an alcohol:acid molar ratio of about 5:1. Similarly, when using a continuously stirred tank reactor conversions of 80% or higher could only be achieved if a similarly much higher alcohol:acid molar ratio was used, e.g. about 5:1 in place of approximately 2:1.

EXAMPLE 6

Using the column reactor of Example 1 monomethyl maleate (MMM) was reacted with dry methanol (MeOH) under the conditions indicated in Table VI, which also lists the results obtained. The mole % conversion figures were obtained by titration.

TABLE VI

| MeOH:MMM molar ratio | 2.6:1 | 2.6:1 |
|---|---|---|
| Residence time (hours) | 3 | 2 |
| Temperature (°C.) | 108 | 111 |

| Tray No. | Mole % conversion | |
|---|---|---|
| 3 | 55.2 | 48.3 |
| 4 | 77.2 | 70.9 |
| 5 | 88.8 | 84.1 |
| 6 | 94.6 | 92.0 |
| 7 | 97.7 | 96.3 |
| 8 | 98.7 | 97.7 |
| 9 | 99.2 | 98.7 |
| 10 | 99.5 | 99.2 |

EXAMPLE 7

The general procedure of Example 6 was followed to yield a product containing, besides a trace of water, substantially pure dimethyl maleate (DMM) but still containing a minor amount of monomethyl maleate (MMM). This product was admixed with dry methanol and passed in cocurrent through a polishing reactor containing Amberlyst 16 similar to reactor 304 of FIG. 6. The results obtained are summarised in Table VII.

TABLE VII

| LHSV (hr⁻¹) | Temperature (°C.) | Mole % Conversion | | Mole % H₂O in feed to reactor | MeOH:ester* molar ratio |
|---|---|---|---|---|---|
| | | In | Out | | |
| 1.0 | 70 | 99.76 | 99.2 | 0.5 | 3.6:1 |
| 1.0 | 70 | 97.61 | 99.5 | 0.2 | 3.4:1 |
| 0.75 | 70 | 97.7 | 99.3 | 0.5 | 3.6:1 |
| 1.0 | 65 | 97.7 | 99.5 | 0.2 | 3.2:1 |

*The term "ester" here applies to the DMM/MMM mixture.

EXAMPLE 8

Using the column reactor of Example 1 the following esterification reactions between the specified acid and the corresponding alcohol component are carried out with similarly good results with the more volatile reactant in each case being supplied to the bottom of the reactor in vapour form and the less volatile component being supplied in liquid form to the second tray of the reactor:

(a) succinic acid and n-propanol to di-n-propyl succinate;
(b) mono-n-butyl maleate and n-butanol to di-n-butyl maleate;
(c) terephthalic acid and methanol to dimethyl terephthalate;
(d) butyric acid and phenol to phenyl butyrate;
(e) glutaric acid and ethanol to diethyl glutarate;
(f) oxalic acid and ethanol to diethyl oxalate;
(g) benzoic acid and ethanol to ethyl benzoate;
(h) 1-naphthoic acid and methanol to methyl 1-naphthoate;
(i) acetic acid and ethylene glycol to ethylene glycol diacetate;
(j) stearic acid and methanol to methyl stearate;
(k) palmitic acid and ethanol to ethyl palmirate;
(l) arachidic acid and methanol to methyl arachidate;
(m) butyric acid and n-nonanol to n-nonyl butyrate;
(n) citric acid and ethanol to ethyl citrate; and
(o) formic acid and propylene glycol to propylene glycol diformate;
(p) oleic acid and iso-propanol to iso-propyl oleate;
(q) ricinoleic acid and methanol to methyl ricinoleate; and
(r) isostearic acid and methyl to methyl isostearate.

We claim:

1. A continuous process for the production of carboxylic acid esters by reaction of a carboxylic acid component selected from a group consisting of mono-, di- and polycarboxylic acids, anhydrides thereof, and mixtures thereof, and of an alcohol component selected from a group consisting of mono-, di- and polyhydric alcohols, phenols and mixtures thereof, in which the carboxylic acid component and alcohol component are passed in countercurrent through an esterification zone maintained under esterification conditions and containing a solid esterification catalyst selected from particulate ion exchange resins having sulphonic acid groups, carboxylic acid groups or both, (i) wherein the esterification zone comprises a column reactor provided with a plurality of esterification trays mounted one above another, each adapted to hold a predetermined liquid volume and a charge of particles of a solid esterification catalyst thereon, liquid downcomer means associated with each esterification tray adapted to allow liquid phase to pass down the column reactor from that esterification tray but to retain the particles of solid esterification catalyst thereon, and vapor upcomer means associated with each esterification tray adapted to allow vapor to enter that esterification tray from below and to agitate and maintain the suspension of the mixture of liquid and solid esterification catalyst on that esterification tray, each esterification tray having a floor that slopes towards a zone of turbulence under said vapor upcomer means to prevent formation of stagnant zones of particles of catalyst thereon, (ii) wherein the less volatile component of the carboxylic acid component and of the alcohol component is supplied in liquid phase to an upper part of the column reactor above the uppermost esterification tray, while the more volatile component of the carboxylic acid component and of the alcohol component is supplied in vapor form beneath the lowermost one of said plurality of esterification trays, (iii) wherein vapor comprising said more volatile component and water of esterification is recovered from an upper part of the column reactor, and (iv) wherein said carboxylic acid ester is recovered from a lower part of the column reactor.

2. A process according to claim 1, wherein the more volatile component is the alcohol component and the less volatile component is the carboxylic acid component.

3. A process according to claim 1 wherein the alcohol component is an alkanol containing from 1 to about 10 carbon atoms.

4. A process according to claim 3, wherein that the alkanol is methanol.

5. A process according to claim 3 wherein the water content of the alkanol vapour supplied to the column reactor is less than about 5 mole %.

6. A process according to claim 1 wherein the carboxylic acid component is an aliphatic monocarboxylic acid or a mixture thereof.

7. A process according to claim 6, wherein the carboxylic acid component is a mixture of fatty acids.

8. A process according to claim 1 wherein the carboxylic acid component is selected from a group consisting of maleic acid, fumaric acid, maleic anhydride, a monoalkyl maleate, a monoalkyl fumarate, and mixtures of two or more thereof.

9. A process according to claim 1 wherein the column reactor is operated at a temperature of from about 80° C. to about 140° C. and at a pressure of from about 1 bar to about 25 bar.

10. A process according to claim 1 wherein the carboxylic acid ester recovered from a lower part of the column reactor is admixed with further alcohol component and is passed through a fixed bed of a solid esterification catalyst.

11. Apparatus for use in the production of a carboxylic acid ester by reaction of a carboxylic acid component selected from a group consisting of mono-, di- and polycarboxylic acids, anhydrides thereof, and mixtures thereof, and of an alcohol component selected from a group consisting of mono-, di- and polyhydric alcohols, phenols and mixtures thereof, comprising a column reactor provided with a plurality of esterification trays mounted one above another, each adapted to hold a predetermined liquid volume and a charge of particles of a solid esterification catalyst thereon, liquid downcomer means associated with each esterification tray adapted to allow liquid phase to pass down the column reactor from that esterification tray but to retain the particles of solid esterification catalyst thereon, vapor upcomer means associated with each esterification tray adapted to allow vapor to enter that esterification tray from below and to agitate and maintain the suspension of the mixture of liquid and solid esterification catalyst on that esterification tray, each esterification tray having a floor that slopes towards a zone of turbulence under said vapor upcomer means to prevent formation of stagnant zones of particles of catalyst thereon, means for supplying the less volatile component of the carboxylic acid component and of the alcohol component in liquid phase to an upper part of the column reactor above the uppermost esterification tray, means for supplying the more volatile component of the carboxylic acid component and of the alcohol component in vapor form to a lower part of the column reactor below the lowermost esterification tray, means for recovering carboxylic acid ester from a lower part of the column reactor below the lowermost esterification tray, and means for recovering from an upper part of the column reactor above the uppermost esterification tray a vaporous stream comprising said more volatile component and water of esterification.

12. Apparatus according to claim 11, in which said vapor upcomer means comprises a sparger positioned so that, in operation, it will lie below the surface of the mixture of liquid and solid esterification catalyst and so that vapor bubbles emerging therefrom will agitate said mixture of liquid and catalyst.

13. Apparatus according to claim 12, in which the sparger is a ring sparger.

14. Apparatus according to claim 12, in which at least one baffle means is mounted in the vicinity of the sparger to enhance the mixing action thereof.

15. Apparatus according to claim 14, in which inner and outer annular baffle means are positioned in the vicinity of the sparger and define an upflow zone in the region of upflowing vapor bubbles and adjacent downflow zones within and outside the upflow zone.

16. Apparatus according to claim 12, in which the vapor upcomer means of at least one esterification tray is provided with a suckback preventer means.

17. Apparatus according to claim 12, in which a screen means is provided on at least one esterification tray to hinder loss of solid esterification catalyst from that esterification tray via its associated downcomer means.

18. Apparatus according to claim 11 further comprising a reactor containing a fixed bed of a solid esterification catalyst connected downstream from the column reactor and means for admixing additional alcohol component with the carboxylic acid ester component recovered from a lower part of the column reactor prior to entry to the further reactor.

\* \* \* \* \*